United States Patent [19]

Zens

[11] 4,172,456
[45] Oct. 30, 1979

[54] ANTI-EMBOLISM STOCKING

[75] Inventor: Charles F. Zens, Milwaukee, Wis.

[73] Assignee: Zens Hosiery Mgf. Co., Inc., Milwaukee, Wis.

[21] Appl. No.: 702,060

[22] Filed: Jul. 2, 1976

[51] Int. Cl.² ............................................. A61F 13/00
[52] U.S. Cl. ........................................ 128/165; 2/240; 66/178 A
[58] Field of Search ............... 128/165, 166, 157, 156; 2/240, 241, 239, 242; 66/178 R, 178 A, 172 E, 190, 197

[56] References Cited

U.S. PATENT DOCUMENTS

| | | | |
|---|---|---|---|
| 940,585 | 11/1909 | Drennan | 66/178 A |
| 1,890,299 | 12/1932 | Mutchler et al. | 66/178 A |
| 2,169,204 | 8/1939 | Hinchliff | 66/172 E |
| 2,213,144 | 8/1940 | McAdams | 66/172 E |
| 2,257,719 | 9/1941 | Smith | 66/172 E |
| 2,277,012 | 3/1942 | Blount | 66/172 E |
| 2,277,766 | 3/1942 | Klumpp | 66/172 E |
| 2,807,946 | 10/1957 | Virchaux | 128/165 X |
| 3,443,404 | 5/1969 | Knohl | 66/178 A |

FOREIGN PATENT DOCUMENTS

| | | | |
|---|---|---|---|
| 703595 | 2/1965 | Canada | 128/165 |
| 97147 | 1/1964 | Denmark | 66/178 A |

*Primary Examiner*—Robert W. Michell
*Assistant Examiner*—Michael H. Thaler
*Attorney, Agent, or Firm*—Michael, Best & Friedrich

[57] ABSTRACT

A full-length, anti-embolism stocking extends over a wearer's leg and is adapted to exhibit a controlled, graduated compressive force on the leg. The compressive force is greatest in the ankle area and diminishes over the length of the stocking to a minimum at the top. Three distinct and defined sections make up the stocking, a lower section covering the calf and foot has a one-way stretch in a circumferential direction, an upper section covering the thigh also has a one-way stretch in a circumferential direction, and an intermediate section covering the knee has a two-way stretch. The knee and calf-foot sections comprise a fabric formed with a jersey stitch incorporating an elastomeric yarn. In the knee section the elastomeric yarn is knit-in to provide the two-way stretch and in the calf-foot section it is laid-in to provide only a one-way, circumferential stretch. The upper thigh section comprises a fabric formed by a rib knit with an elastomeric yarn laid-in to provide a one-way stretch in a circumferential direction. The elastomeric yarn is laid-in and knit-in under tension and the tension is varied to vary the amount of elastomeric yarn going into the stocking from a minimum in the foot-ankle area to a maximum in the upper thigh section to provide the graduated compressive force.

4 Claims, 4 Drawing Figures

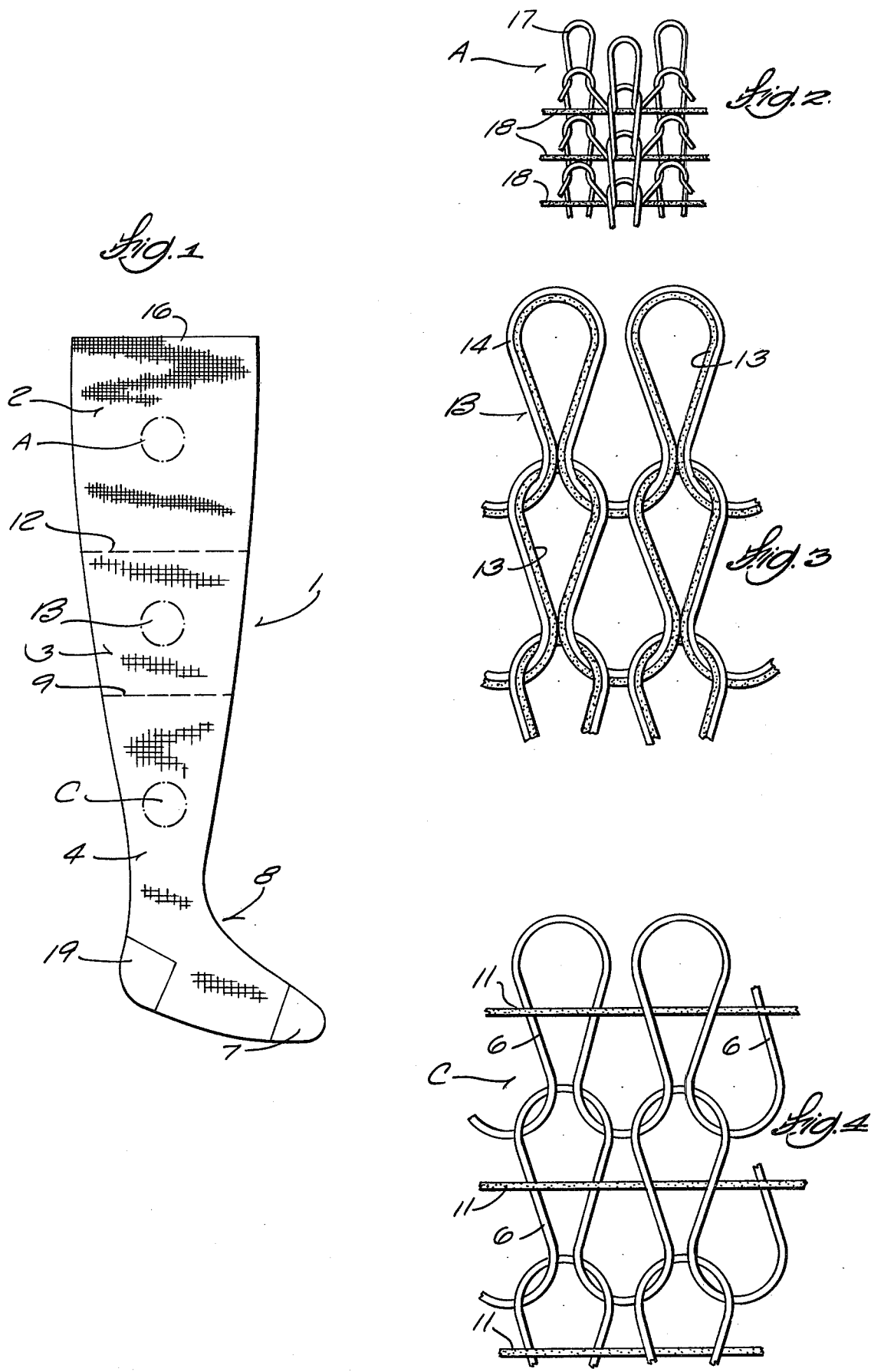

ANTI-EMBOLISM STOCKING

BACKGROUND OF THE INVENTION

This invention relates to therapeutic stockings.

Support stockings are used by individuals who are generally immobilized to protect them against thrombus formation and possible embolisms. Support stockings are also used by individuals suffering from varicose veins. Such support stockings generally are made up of a combination of base and elastomeric yarns, the latter being included to achieve a desired degree of compressive force around the wearer's leg. These concepts are generally well known and various stocking constructions have been proposed in the past.

This invention is concerned with the provision of a therapeutic stocking and has as one of its general objects to provide a stocking which will exert a graduated compressive force on the wearer's leg decreasing from a maximum in the foot-ankle area through to a minimum at the top of the stocking in the thigh area.

Another object is to provide a stocking construction wherein the graduated compressive force is achieved while also maintaining desired characteristics in the knee area, i.e. to prevent the stocking from sagging in the knee area or exerting a downward pull on the thigh portion when the wearer's knee is bent.

A further object of this invention is to knit the fabric for the stocking in a most economical, expeditious manner.

SUMMARY OF THE INVENTION

For the achievement of the above and other objects, this invention proposes a full-length stocking having a combination of base and elastomeric yarns stitched such that a graduated compressive force will be exerted on the wearer's leg. The compressive force varies from a maximum in the foot-ankle area to a minimum at the top of the stocking in the thigh area.

Preferably, the stocking includes a knee section having two-way stretch characteristics to prevent sagging in the knee area and reducing a pull on the thigh section of the stocking when the knee is bent. This is preferably accomplished by forming the knee area with the elastomeric yarn being knit-in with the base yarn in a conventional jersey hoisery stitch.

A lower leg section extends from the knee area through the calf and ankle area and consists of a fabric made with a conventional jersey hoisery stitch with an elastomeric yarn laid-in with the base yarn. An upper leg section, which is intended to extend from the knee area to cover the wearer's thigh, consists of a fabric which is rib stitched with an elastomeric yarn laid-in with the base yarn of the conventional rib stitch. The rib stitch cooperates in holding the overall stocking up and the elastomeric yarn in the upper leg section, as well as in the knee and lower leg sections, provides the desired compressive force on the wearer's leg.

Preferably, the graduated compressive force is achieved by measuring the amount of elastomeric yarn which is included in the various areas of the fabric. The amount of elastomeric yarn is measured by feeding the elastomeric yarn into the fabric under varying amounts of tension. More specifically, in the foot-ankle area, where the compressive force is to be the greatest, the yarn is fed in under the highest tension so that less elastomeric yarn will be present in the foot-ankle area. This will cause a greater contraction of the fabric in the area and will exert a greater compressive strength when it is expanded around the wearer's foot and ankle. The tension on the elastomeric yarn as it is fed into the fabric is then decreased as the knitting operation proceeds from the foot-ankle area throughout the length of the stocking and reaches a minimum at the stocking top.

This results in three distinctly separate stocking sections wherein two sections, the knee and calf-foot-ankle sections, are knit in a continuous manner and the thigh section is knit separately and sewn to the other two.

Other objects and advantages will be pointed out in, or be apparent from, the specification and claims, as will obvious modifications of the embodiment shown in the drawings, in which:

FIG. 1 is a side elevation of a stocking constructed in accordance with this invention;

FIG. 2 is an enlarged view of portion A of the stocking of FIG. 1 illustrating the knit of the fabric in the thigh section of the stocking;

FIG. 3 is an enlarged view of portion B illustrating the knit of the fabric in the knee section of the stocking; and FIG. 4 is an enlarged view of portion C illustrating the knit of the fabric in the lower leg, calf-ankle-foot, section of the stocking.

DESCRIPTION OF THE PREFERRED EMBODIMENT

With particular reference to the drawings, a full-length therapeutic stocking 1 includes three distinct sections 2, 3, and 4. Section 2 covers the upper leg thigh area, section 3 covers the knee area and section 4 covers the calf-ankle-foot area of a wearer.

In the preferred embodiment, section 4 consists of a fabric constructed with a conventional jersey hoisery stitch made up of base yarn 6, which is conventionally made of nylon, cotton, etc. Section 4 extends from toe portion 7 through the ankle area 8 to a line 9 beneath section 3. Section 4 is provided with a one-way stretch in a circumferential direction so as to be capable of exerting a compressive force around the wearer's leg. The one-way circumferential stretch is provided by elastomeric yarn 11 which is laid-in, which is sometimes referred to as floated, in the jersey stitch.

Elastomeric yarn 11 is laid-in, not knit-in so that a basic one-way stretch is provided in a circumferential direction relative to the longitudinal axis of the stocking and the wearer's leg. This one-way stretch will exert a compressive force around the wearer's leg and the amount of that compressive force is graduated by varying the amount of the elastomeric yarn which is laid-in as the jersey stitch is made. This may be referred to as measuring the amount of the elastomeric yarn which is so laid-in and is accomplished by feeding the elastomeric yarn into the jersey stitch under tension and varying the amount of tension to vary the amount of yarn laid-in. More specifically, the tension is to be greatest in the foot-ankle area and in that area the elastomeric yarn is laid-in under maximum tension. The tension is then gradually reduced as the yarn is laid-in along the length of section 4 up to line 9. The elastomeric yarn which was laid-in under the greatest tension will contract to the smallest circumference when relaxed and thus exert the greatest compressive force on the wearer's leg when stretched over the leg.

The variation in the tension in the elastomeric yarn as it is laid-in is accomplished mechanically in a conventional manner and the machine for accomplishing this is well known so is neither illustrated nor described.

Section 3, similar to section 4 consists of a fabric which is also made with a conventional jersey hoisery stitch and extends from line 9 to a second line 12. Section 3 is intended to cover the wearer's knee. When the wearer's knee is bent, it tends to cause the fabric in section 3 to gather and sag. In addition, bending the knee can result in a downward pull on section 2 which would tend to cause the entire stocking to sag. In order to counteract these undesirable characteristics, this invention proposes that the fabric of section 3 be provided with a two-way stretch, i.e. be capable of stretching in both a circumferential and axial direction. As illustrated in FIG. 3, this is achieved by having elastomeric yarn 13 knit-in with the base yarn 14. With the two-way stretch, the knee can be bent without causing a sag in the knee area and without exerting any appreciable downward pull on section 2.

Again in section 3, elastomeric yarn 13 is measured into the jersey stitch under varying tension, the tension decreasing from line 9 to line 12. This then accomplishes a decreasing compressive force around the wearer's knee from line 9 to line 12.

From line 12 to the open end 16 of stocking 1, section 2 is formed of a fabric made with a conventional rib stitch. This is illustrated in FIG. 2. Base yarn 17 forms the basic rib stitch and elastomeric yarn 18 is laid-in with the rib stitch. The rib stitch, in a well known manner, provides some expansion and contraction characteristics in both an axial and circumferential direction tending to hold the stocking up on the wearer's leg. The elastomeric yarn attributes basically a one-way circumferential stretch to the section 2 to provide for a compressive force on the wearer's thigh. The amount of elastomeric yarn 18 laid-in with the base yarn 17 in section 2 is varied from a minimum at line 12 to a maximum at the open end 16 by decreasing the tension under which elastomeric yarn 18 is laid-in from line 12 to open end 16.

This stocking construction thus provides three separate and distinct stocking sections and overall provides a compressive force around the wearer's leg varying from a maximum in the foot-ankle area 8 through to a minimum at the open end 16.

Preferably, sections 3 and 4 are knit in a continuous manner. Section 2 is knit separately on a ribber and sewn to the top of section 3 with a conventional over edge seam (not shown).

It should also be noted that the number of stitches per course is increased appreciably in section 2 as compared to sections 3 and 4. For example, 480–600 stitches per course are preferably provided in section 2 whereas approximately 400 stitches per course are provided in sections 3 and 4. This is to enhance the inherent stretch and ability of section 2 to grasp the thigh in a manner to hold the stocking up, and accommodate the general increase in size encountered in a wearer's thigh. Basically, this increase in stitches per course is accomplished by knitting section 2 separately on a ribber. It should be appreciated, however, that knitting the entire stocking in a continuous manner is broadly within the scope of this invention.

The top 16 of the stocking is completed by turning over an approximate 1 inch length of fabric and sewing it off to provide a double thickness at the top. The basic rib knit tends to hold the stockings up without an auxiliary garter, the double thickness band at the top 16 further cooperates to that end.

A heel portion 19 is formed in the stocking in a conventional manner.

Although but one embodiment of the present invention has been illustrated and described, it will be apparent to those skilled in the art that various changes and modifications may be made therein without departing from the spirit of the invention or from the scope of the appended claims.

I claim:

1. A full-length therapeutic stocking adapted to extend over and cover a wearer's leg and exhibit a graduated compressive force on the leg diminishing from a maximum in the foot-ankle area through a minimum in the upper thigh area, said stocking characterized in that the fabric thereof comprises:

first and second separate and distinct generally tubular sections at the opposite ends thereof and an intermediate separate and distinct generally tubular section knit of a base yarn and located to cover the wearer's knee and connecting said first and second tubular sections to form an elongated stocking, said second tubular section covering substantially all of the wearer's thigh, an elastomeric yarn incorporated in said first and second sections so that said first and second sections exhibit substantially one-way stretch in a circumferential direction, said elastomeric yarn being knit-in to said fabric with said base yarn of said intermediate section to extend around the entire circumference of said intermediate section so that said intermediate section exhibits a two-way stretch, the amount of elastomeric yarn varying from a minimum amount at the end of said first section remote from said intermediate section to a maximum at the end of said second section remote from said intermediate section so that said stocking exhibits graduated compressive force when stretched around the circumference of a wearer's leg which compressive force varies from a maximum at said remote end of said first section to a minimum at said remote end of said second section.

2. The therapeutic stocking of claim 1 wherein said first and second sections are knit of a base yarn and include an elastomeric yarn laid-in said fabric with said base yarn so that said first and second sections exhibit said substantially one-way stretch in a circumferential direction.

3. The therapeutic stocking of claim 1 wherein said first and intermediate sections comprise a knit fabric made with a jersey hoisery stitch and said second section comprises a knit fabric made with a rib stitch.

4. A full-length therapeutic stocking comprising, in combination;

a lower generally tubular portion forming a foot-ankle-calf section, a generally tubular knee section connected to and extending from said foot-ankle-calf section, a generally tubular thigh section connected to and extending from said knee section to an open end, and covering substantially all of the wearer's thigh, said foot-ankle-calf section comprising a fabric made with a jersey stitch and including a laid-in-elastomeric yarn, the amount of said elastomeric yarn varying from a minimum in the foot-ankle portion of said foot-ankle-calf section to a maximum at the end thereof which is connected to said knee section, said knee section comprising a fabric made with a jersey stitch and including an elastomeric yarn knit-in said fabric to extend around the entire circumference of said knee section to provide a two-way stretch, the amount of said elastomeric yarn in said knee section varying from a minimum at the connection with said foot-ankle-calf section to a maximum at the connection with said thigh section, and said thigh section comprising a fabric made with a rib stitch and including an elastomeric yarn laid-in said rib stitch, said elastomeric yarn varying from a minimum amount at the connection to said knee portion to a maximum amount at the top of said thigh portion.

* * * * *